United States Patent [19]

Sims et al.

[11] Patent Number: 5,744,071
[45] Date of Patent: Apr. 28, 1998

[54] PROCESSES FOR PREPARING ALKYNYL KETONES AND PRECURSORS THEREOF

[75] Inventors: Philip Franklin Sims, Cherryville; Anne Pautard-Cooper, Gastonia, both of N.C.

[73] Assignee: FMC Corporation, Philadelphia, Pa.

[21] Appl. No.: 752,684

[22] Filed: Nov. 19, 1996

Related U.S. Application Data

[60] Provisional application No. 60/006,967 Nov. 20, 1995.
[51] Int. Cl.⁶ .................................. C07F 1/02; C07F 3/02
[52] U.S. Cl. .................................. 260/665 R; 260/665 G; 568/309; 568/319; 568/383; 568/397; 568/398
[58] Field of Search ........................... 260/665 R, 665 G; 528/319, 309, 383, 397, 398

[56] References Cited

U.S. PATENT DOCUMENTS 3,410,918   11/1968   Beumel et al. .
5,626,798   5/1997   Schwindeman et al. ........... 260/665 R

OTHER PUBLICATIONS

H.D. Verkruijsse, et al., J. Organometallic Chem. 338: 289–294 (1988).
L. Brandsma, "Preparative Acetylenic Chemistry" (Elsevier 2d ed. 1988), pp. 24–25, 36–38; 105–106.

*Primary Examiner*—Paul F. Shaver
*Attorney, Agent, or Firm*—Bell Seltzer Intellectual Property Law Group of Alston & Bird LLP

[57] ABSTRACT

The present invention provides processes for making alkynyl ketones and precursors thereof, using less expensive reagents and/or hydrocarbon solvents and/or higher temperatures.

42 Claims, No Drawings

PROCESSES FOR PREPARING ALKYNYL KETONES AND PRECURSORS THEREOF

CROSS-REFERENCE TO RELATED APPLICATIONS

This application is related to commonly owned copending Provisional Application Ser. No. 60/006,967, filed Nov. 20, 1995, and claims the benefit of its earlier filing date under 35 U.S.C. 119(e).

FIELD OF THE INVENTION

This invention relates to processes for making metallated alkynyl compounds and for making alkynyl ketones using the same.

BACKGROUND OF THE INVENTION

Alkali metal and alkaline earth metal acetylenes are useful precursors in the synthesis of organic compounds. These compounds typically are highly reactive with ketones, labile chlorides, and the like. For example, 1-propynyl lithium ($CH_3$—C≡C—Li) is a useful precursor of 2-phenethyl 1-propynylketone (PPK), an acetylenic ketone, which is employed in the synthesis of a protease inhibitor.

Various techniques can be used to prepare propynyl lithium and other lithiated acetylenes. For example, the propynyl anion can be prepared by the reaction of propyne ($CH_3$—C≡CH) with an organolithium compound in a mixed hydrocarbon/ethereal solvent. See L. Brandsma, *"Preparative Acetylenic Chemistry"* (Elsevier 2d ed. 1988), page 24. U.S. Pat. No. 3,410,918 describes passing a gaseous mixture of propyne and allene through a slurry of lithium metal and sodium metal to produce propynyl lithium.

These techniques can require expensive reagents, such as propyne, or reagents which are difficult to handle, particularly on a commercial scale, such as lithium metal, which is a pyrophoric solid. This can also limit the commercial viability of these and other prior processes.

These processes also typically require an ethereal solvent, such as tetrahydrofuran (THF), to solubilize the resultant lithiated acetylene product. However, ethereal solvents such as THF can be expensive, particularly as the reaction is scaled up to commercial production levels. In addition, ethers such as THF are highly reactive with alkyl lithium starting reagents. Accordingly, these reactions typically require very low temperatures ($-20°$ C. and lower). However, many reactor systems in production facilities do not have the capability to cool to these temperatures, and installation of reactor systems capable of cooling to these low temperatures require increased capital investments. This can adversely impact commercial scale production of organic products from both an engineering and economic standpoint.

Propynyl ketones can be prepared using a propynyl lithium precursor by a cationic exchange reaction with zinc chloride, followed by coupling of the propynyl anion with a derivative of a carboxylic acid in a hydrocarbon/ethereal solvent to yield the desired product. Typically, the reaction is conducted at a temperature ranging from about $-20°$ C. to about $0°$ C. After addition is complete, the reaction is warmed to room temperature (about $20°$ C.) for 30 minutes or more. See Brandsma, supra, page 105; L. Brandsma et al., *J. Organometallic Chem.* 388: 289–294 (1988).

Propynyl ketones, such as PPK, produced under these conditions can contain impurities. As a result, the product may require downstream purification, such as vacuum distillation at high temperatures. However, propynyl ketones such as PPK can rapidly decompose when heated above about $150°$ C. in an exothermic reaction.

SUMMARY OF THE INVENTION

A first aspect of the present invention is a process for making metallated acetylenes, in which a mixture of at least one acetylenic compound and at least one saturated or unsaturated hydrocarbon (which is different from the acetylenic compound) is contacted with an organometallating agent capable of deprotonating and metallating the acetylenic compound, such as an organolithium. An exemplary mixture is MAPP gas, a gaseous byproduct of butadiene production which includes propyne, allene, propene and saturated hydrocarbons, such as propane and butane. Another exemplary mixture includes propyne and a saturated hydrocarbon, such as propane.

In contrast with prior processes, the process in accordance with this aspect of the invention uses a relatively inexpensive reagent (the acetylenic compound mixture) as a starting reagent. Further, the process eliminates the use of reagents which are difficult to handle, particularly on a commercial scale, such as lithium metal. Accordingly, the process can improve the commercial viability of preparing metallated acetylenic compounds on a large scale.

From the literature, it would be expected that an organolithium would deprotonate other unsaturated hydrocarbons present in the mixture, not just propyne. See L. Brandsma, *"Preparative Acetylenic Chemistry"* (Elsevier 2d ed. 1988), page 233, which states that butyllithium can metallate allenes. Surprisingly, however, the inventors have not observed allenyl and/or propenyl derived products.

A second aspect of the present invention is a process for making metallated acetylenes, in which a relatively pure acetylenic compound or a mixture thereof with at least one saturated or unsaturated hydrocarbon (such as MAPP gas) is reacted with an organometallating agent capable of deprotonating and metallating the acetylenic compound, such as an organolithium, in a hydrocarbon solvent. As noted above, prior processes typically require an ethereal solvent to solubilize the metallated compound. However, ethers such as THF are highly reactive with organolithium starting reagents, and processes using ethereal solvents require very low reaction temperatures ($-20°$ C. and lower).

In contrast, in this aspect of the invention, ethereal solvents, and accordingly low reaction temperatures, are eliminated. This can improve economies of synthesis, both with regard to the cost of materials and specialized equipment required to conduct synthesis at extremely low temperatures.

A third aspect of the invention is a process for preparing acetylenic ketones in which a metallated acetylene is reacted with transition metal halide or other suitable transition metal derivative (optionally) and with a derivative of carboxylic acid to form a reaction product. The inventors have found that the reaction product includes unreacted reagents, such as unreacted carboxylic acid derivatives, in addition to the acetylenic ketone. The inventors have also found that the unreacted reagents can participate in undesirable side reactions and thus adversely impact purity of the recovered ketone. For example, unreacted carboxylic acid derivatives can cleave ethereal solvents in the presence of catalytic amounts of zinc halide, particularly at work-up temperatures currently recommended in the literature.

In this aspect of the invention, the reaction product is treated under conditions sufficient to minimize or eliminate formation of impurities by unreacted starting reagents during work-up of the reaction product and recovery of the acetylenic ketone. Suitable neutralizing agents are added to the reaction product to neutralize unreacted reagents at temperatures below which the unreacted reagents can form impurities. This can provide a three to four fold reduction of impurities in the recovered acetylenic ketone. Because the recovered product is purer, additional downstream purification steps can be minimized or eliminated. This is advantageous because downstream purification, such as distillation, can increase production costs and time and adversely affect product quality.

DETAILED DESCRIPTION OF THE INVENTION

The term "metallated acetylenes" as used herein refers to compounds of the formula R—C≡C—M, in which R is hydrogen, alkyl, cycloalkyl, aryl, alkylaryl, arylalkyl, silyl or heteroaromatic, and M is an alkali or alkaline earth metal, such as, but not limited to, lithium, sodium, and magnesium. As used herein, the term "alkyl" refers to C1 to C10 linear or branched alkyl, such as, but not limited to, methyl, ethyl, propyl, butyl, isopropyl, n-butyl, s-butyl, t-butyl, pentyl, hexyl, and the like. The term "aryl" as used herein refers to C6 to C10 cyclic aromatic groups such as phenyl, naphthyl, and the like and includes substituted aryl groups such as tolyl. The term "cycloalkyl" as used herein refers to C3 to C8 cyclic alkyl, such as cyclopropyl, cyclobutyl, cyclopentyl, cyclohexyl, and the like. The term "silyl" as used herein refers to C1 to C10 organosilicon groups, such as trimethylsilyl and the like. The term "heteroaromatic" as used herein refers to C4 to C10 heteroaromatic groups, such as pyridinyl, furanyl thiophenyl, and the like.

In one aspect of the invention, metallated acetylenes are prepared by the reaction of an organometallating agent capable of deprotonating and metallating the acetylenic compound with a mixture comprising at least one acetylenic compound and at least one other hydrocarbon which is different from the acetylenic compound. Exemplary organometallating agents include without limitation organoalkali metal compounds, organoalkaline earth metal compounds, organomagnesium halides, and the like. Organoalkali metal compounds, such as organolithium and organosodium, generally can be described by the formula $R^1$—M, in which $R^1$ is alkyl, cycloalkyl, aryl, alkylaryl, or arylalkyl, each of which is defined above with regard to R, and M is alkali metal, such as lithium or sodium. Organoalkaline earth metal compounds, such as dialkylmagnesium, generally can be described by the formula $M(R^1)_2$, in which each $R^1$ is as defined above and M is alkaline earth metal, such as magnesium. Organomagnesium halide can generally be described as a Grignard reagent $R^1MgX$, in which $R^1$ is as defined above and X is halide.

The acetylenic compound may be any compound which includes a reactive acetylenic linkage —C≡CH, and generally can be described by the formula R—C≡CH, wherein R is as defined above.

The acetylenic compound is provided as a component of a mixture with at least one other hydrocarbon which is different from the acetylenic compound. The other hydrocarbon can be a saturated or unsaturated, branched or linear hydrocarbon.

An exemplary mixture includes allene ($H_2C:C:CH_2$) and/or propene. Saturated linear or branched C1 to C4 hydrocarbons can also be present in the mixture, including, for example, propane and butane. Advantageously, the mixture is a gaseous mixture comprising propyne and allene known as MAPP gas. MAPP gas is widely available commercially as a by-product of the manufacture of butadiene, and is generally used as a welding fuel gas.

The composition of the mixture can vary, so long as the mixture includes acetylenic compound in an amount sufficient to produce lithiated acetylenic compound. Suitable MAPP gases comprise about 2% to about 40% propyne and about 1% to about 40% allene. The MAPP gas can also include about 1% to about 20% propene. Commercially available MAPP gas also typically includes about 20% to about 60% saturated C1 to C4 hydrocarbons, principally propane and butane, as diluents. Surprisingly, no allenyl or propenyl derived products are observed when using MAPP gas.

Another exemplary mixture comprises propyne and at least one saturated hydrocarbon, for example about 15% or less propane.

The mixture of acetylenic compound and at least one saturated and/or unsaturated hydrocarbon is contacted with the organometallating agent in a mixed ethereal/hydrocarbon solvent at a temperature of less than or about −20° C. The mixture can be added to the organometallating agent (such as a solution of alkyllithium), the organometallating agent added to the mixture, or the reagents added to a reaction vessel substantially simultaneously. The reaction product, which includes metallated acetylenic compound, can be allowed to reach room temperature after the reaction is complete, and the metallated acetylenic compound can be recovered using conventional techniques.

Suitable hydrocarbon solvents include, but are not limited to, alkanes, cycloalkanes and aromatic solvents, such as alkanes and cycloalkanes containing five to ten carbon atoms, such as pentane, hexane, cyclohexane, methylcyclohexane, heptane, methylcycloheptane, octane, decane and the like, and aromatic solvents containing six to ten carbon atoms such as toluene, ethylbenzene, p-xylene, m-xylene, o-xylene, n-propylbenzene, isopropylbenzene, n-butylbenzene, t-butylbenzene, and the like, and mixtures thereof. Suitable ethereal solvents include, but are not limited to, diethyl ether, dibutyl ether, tetrahydrofuran (THF), 2-methyltetrahydrofuran, methyl tert-butyl ether, and the like, and mixtures thereof.

The amount of ether present in the solvent can vary depending, for example, on the solubility of the reagents and/or the resultant metallated acetylenic compound, the temperature of the reaction, and the like. Exemplary solvents include mixed ethereal/hydrocarbon solvents of tetrahydrofuran and hexane, methyl tert-butyl ether and hexane, and the like.

An exemplary reaction in accordance with this aspect of the invention is illustrated below:

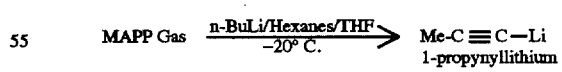

$$\text{MAPP Gas} \xrightarrow[-20°\text{C.}]{\text{n-BuLi/Hexanes/THF}} \text{Me-C}\equiv\text{C—Li}$$
1-propynyllithium Metallated acetylenic compounds of the formula R—C≡C—M described above, in which R and M are as defined above, can also be prepared in the absence of an ethereal solvent and/or at increased temperatures relative to conventional processes. In this aspect of the invention, a suitable source of an acetylenic compound is reacted with an organometallating agent as described above, such as an alkyllithium. Suitable acetylenic compound sources include relatively pure acetylenic compounds of the formula R—C≡CH, as defined above, such as propyne gas. The acetylenic compound can also be provided as a mixture of the acetylenic compound with at least one other hydrocarbon as described above, for example, MAPP gas and propyne/propane mixtures.

The acetylenic compound can be added to the organometallating agent (such as a hydrocarbon solution of an alkyllithium), the organometallating agent can be added to the acetylenic compound, or the reagents added to a reaction vessel substantially simultaneously. The hydrocarbon solvent can be any of the hydrocarbon solvents described above. In addition, the reaction can be conducted at a temperature of at least about 0° C. or higher.

An exemplary reaction in accordance with this aspect of the invention is illustrated below:

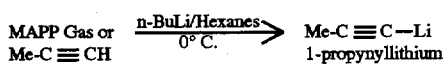

Metallated acetylenic compounds produced in accordance with the present invention can be further reacted with suitable reagents, such as derivatives of carboxylic acid and salts thereof, to form acetylenic ketones of the formula $RC\equiv CC(=O)R^2$. A metallated acetylene (prepared as described above or by other processes) is optionally reacted with transition metal halide or other suitable transition metal derivative in the presence of an ethereal cosolvent. The acetylenic organometallic compound is then reacted with a derivative of carboxylic acid of the formula $R^2COX$ or a salt thereof. The reaction takes place at a temperature less than or about –20° C. for a period sufficient to produce acetylenic ketone. See L. Brandsma, *Preparative Acetylenic Chemistry* (Elsevier 2d ed. 1988), page 105; L. Brandsma, et al., *J. Organometallic Chem.* 388, 289–294 (1988).

Exemplary transition metal halides include, but are not limited to, zinc chloride, zinc bromide, manganese chloride, cadmium chloride, and the like. Other transition metal derivatives can also be used.

$R^2$ is selected from the group consisting of alkyl, aryl, alkylaryl, arylalkyl, or cycloalkyl (each as defined above) and X is halogen, C1 to C10 alkoxy, anhydride, or $NR^3R^4$, wherein each $R^3$ and $R^4$ is independently selected from alkyl, aryl, alkylaryl, arylalkyl, cycloalkyl (each as defined above), C1 to C10 alkoxy, or $R^3$ and $R^4$ together represent a heterocyclic group (such as imidazole, triazole, oxazolidiene, and the like). The transition metal halide, or other suitable transition metal derivative, is an optional reagent, and the metallated acetylene can be reacted directed with a derivative of carboxylic acid or a salt thereof.

Exemplary acid derivatives include, but are not limited to, hydrocinnamoyl chloride, acetyl chloride, benzoyl chloride, Weinreb amide of hydrocinnamic acid (in which X is $N(OCH_3)CH_3$), and the like, although other acid derivatives or their salts can be used.

Exemplary acetylenic ketones include, without limitation, 2-phenethyl 1-propynylketone (PPK), phenyl propynyl ketone, cyclohexyl 1-butynyl ketone, isopropyl 1-butynyl ketone, cyclohexyl 2-trimethylsilylethynyl ketone, and the like.

After the reaction is substantially complete, the reaction product, which includes acetylenic ketone and unreacted starting reagents such as acid derivative, is treated to neutralize and thus reduce or minimize unreacted starting reagents. During the neutralization step, the reaction product is maintained at reduced temperatures of less than about 0° C., preferably between about –20° C. and about 0° C., to minimize the reactivity of unreacted starting reagents and thus improve the purity of the recovered ketone. The reaction product can be warmed up to about 0° C. for not more than 1 hour during the neutralizing step.

The types and quantities of unreacted starting reagents present in the reaction product can be determined using conventional techniques, and suitable neutralizing agents can be added to the reaction product as needed in amounts sufficient to substantially neutralize unreacted reagents. For example, exemplary neutralizing agents for neutralizing acid derivative include, without limitation, alkali and alkaline earth metal hydroxides (such as sodium hydroxide NaOH, potassium hydroxide KOH, calcium hydroxide $Ca(OH)_2$ and the like), ammonium hydroxide, alkali and alkaline earth metal carbonates or bicarbonates (such as potassium carbonate $K_2CO_3$, sodium bicarbonate $NaHCO_3$, and the like), water, or other suitable agents known in the art for quenching acid. Other neutralizing agents may be added to the reaction product as well, depending upon the unreacted starting agents present.

Neutralizing unreacted reagents at low temperatures prior to work-up and recovery of the acetylenic ketone can improve the purity of the recovered product to at least about 80% purity, and more preferably at least about 90% purity, and higher. In contrast, following conventional techniques, the recovered product has a purity of only about 80% (as illustrated in comparative example 2 below), and the product requires downstream purification steps. Further, the process of the invention can provide improved purity with improved yield (at least about 75% yield and higher).

An exemplary reaction in accordance with this aspect of the invention is illustrated below:

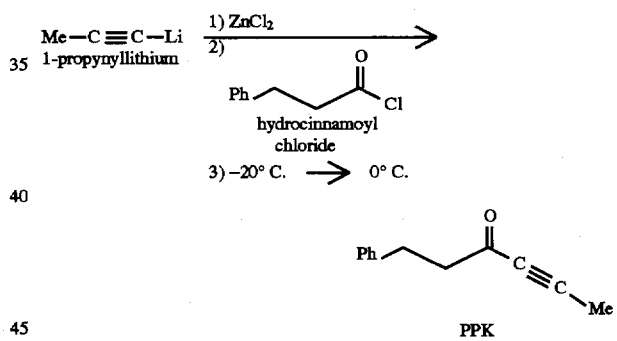

The following examples further illustrate the invention.

EXAMPLE 1

To a 250 ml 3-neck flask under argon is added 50 grams 24% w/w n-Butyllithium (n-BuLi) (0.19 mol). The flask is then cooled to below –20° C. followed by addition of 75 ml THF. To this solution cooled to below –20° C. is added MAPP gas (about 50 grams or until all n-BuLi is consumed). In another 500 ml 3-neck flask under argon 86 ml of THF is added. At 0° C. 25.5 grams $ZnCl_2$ (0.19 mol) is added. The propynyllithium slurry is then added to the flask containing $ZnCl_2$ and stirred for 30 minutes. This solution is then cooled to –20° C. and 26.3 grams hydrocinnamoyl chloride (0.16 mol) is added and solution is stirred for 1 hour at 0° C. After workup and concentration at reduced pressure 2-phenethyl 1-propynylketone is obtained in 78% yield and 93% purity.

Comparative Example 2

To 250 ml 3-neck flask under argon is added 50 grams 24% w/w n-BuLi (0.19 mol). Flask is then cooled to below −20° C. followed by addition of 75 ml THF. To this solution cooled to below −20° C. is added MAPP gas (about 50 grams or until all n-BuLi is consumed). In another 500 ml 3-neck flask under argon is added 86 ml of THF. At 0° C., 25.5 grams $ZnCl_2$ (0.19 mol) is added. The propynyllithium slurry is then added to the flask containing $ZnCl_2$ and stirred for 30 minutes. To this solution at 0° C. is added 26.3 grams hydrocinnamoyl chloride (0.16 mol) followed by warming to 20° C. or higher. After workup and concentration at reduced pressure 2-phenethyl 1-propynylketone is obtained in 70% yield and 80% purity.

EXAMPLE 3

To 250 ml 3-neck flask under argon is added 50 grams 24% w/w n-BuLi (0.19 mol). Flask is then cooled to below −20° C. followed by addition of 75 ml THF. To this solution cooled to below −20° C. is added propyne until all n-BuLi is consumed. In another 500 ml 3-neck flask under argon is added 86 ml of THF. At 0° C. 25.5 grams $ZnCl_2$ (0.19 mol) is added. The propynyllithium slurry is then added to the flask containing $ZnCl_2$ and stirred for 30 minutes. This solution is then cooled to −20° C. and 26.3 grams hydrocinnamoyl chloride (0.16 mol) is added and solution is stirred for 1 hour at 0° C. After workup and concentration at reduced pressure 2-phenethyl 1-propynylketone is obtained in 78% yield and 93% purity.

EXAMPLE 4

To 500 ml 3-neck flask under argon is added 50 grams 24% w/w n-BuLi (0.19 mol). To this solution was added 150 ml hexane and cooled to 0° C. followed by addition of MAPP gas (about 50 grams or until all n-BuLi is consumed). At 0° C. 75 ml THF followed by 25.5 grams $ZnCl_2$ (0.19 mol) is added and stirred for 30 minutes. This solution is then cooled to −20° C. and 26.3 grams hydrocinnamoyl chloride (0.16 mol) is added and solution is stirred for 1 hour at 0° C. After workup and concentration at reduced pressure 2-phenethyl 1-propynylketone is obtained in 78% yield and 90% purity.

EXAMPLE 5

To 250 ml 3-neck flask under argon is added 50 grams 24% w/w n-BuLi (0.19 mol). Flask is then cooled to below −20° C. followed by addition of 130 ml THF. To this solution cooled to below −20° C. is added propyne until all n-BuLi is consumed. At 0° C., 25.5 grams $ZnCl_2$ (0.19 mol) is added and stirred for 30 minutes. This solution is then cooled to −20° C. and 26.3 grams hydrocinnamoyl chloride (0.16 mol) is added and solution is stirred for 1 hour at 0° C. After workup and concentration at reduced pressure 2-phenethyl 1-propynylketone is obtained in 78% yield and 93% purity.

EXAMPLE 6

To 250 ml 3-neck flask under argon is added 50 grams 24% w/w n-BuLi (0.19 mol). Flask is then cooled to below −20° C. followed by addition of 75 ml THF. To this solution cooled to below −20° C. is added propyne until all n-BuLi is consumed. In another 500 ml 3-neck flask under argon is added 70 ml of THF followed by 39.5 grams hydrocinnamoyl chloride (0.285 mol). At 0° C. the propynyllithium slurry is then added to the flask containing hydrocinnamoyl chloride and is stirred for 1 hour at 10° C. After workup and concentration at reduced pressure 2-phenethyl 1-propynylketone is obtained in 78% yield and 80% purity.

The foregoing examples are illustrative of the present invention and are not to be construed as limiting thereof. The invention is defined by the following claims, with equivalents of the claims to be included therein.

That which is claimed is:

1. A process for making metallated acetylenes, comprising contacting a mixture comprising at least one acetylenic compound and at least one saturated or unsaturated hydrocarbon which is different from said at least one acetylenic compound with an organometallating agent under conditions sufficient to produce metallated acetylenic compound.

2. The process of claim 1, wherein said acetylenic compound is a compound according to the formula R—C≡CH, said organometallating agent is selected from the group consisting of organoalkali metals, organoalkaline earth metals, and organomagnesium halides, and said metallated acetylenic compound is a compound according to the formula R—C≡C—M, wherein R is hydrogen, alkyl, cycloalkyl, aryl, alkylaryl, arylalkyl, silyl, or heteroaromatic, and M is alkali metal or alkaline earth metal.

3. The process of claim 2, wherein said organometallating agent is an organoalkali metal compound of the formula $R^1$—M, wherein $R^1$ is alkyl, cycloalkyl, aryl, alkylaryl, or arylalkyl and M is alkali metal.

4. The process of claim 3, wherein each of R and $R^1$ is alkyl and M is lithium.

5. The process of claim 1, wherein said at least one saturated or unsaturated hydrocarbon is allene.

6. The process of claim 5, wherein said mixture further comprises at least one saturated C1 to C4 hydrocarbon.

7. The process of claim 6, wherein said C1 to C4 hydrocarbon is propane, butane, or a mixture thereof.

8. The process of claim 1, wherein said mixture comprises about 2% to about 40% propyne; about 1% to about 40% allene; about 20% to about 60% propane and butane.

9. The process of claim 1, wherein said mixture comprises about 85% to about 99% propyne and about 1% to about 15% propane.

10. The process of claim 1, wherein said mixture is contacted with said organometallating agent in a mixed ethereal/hydrocarbon solvent.

11. The process of claim 10, wherein said mixed ethereal/hydrocarbon solvent comprises tetrahydrofuran and hexane.

12. The process of claim 10, wherein said mixed ethereal/hydrocarbon solvent comprises methyl tert-butyl ether and hexane.

13. The process of claim 1, wherein said contacting step is conducted at a temperature of about −20° C. or less.

14. The process of claim 13, further comprises after said contacting step the step of heating said metallated acetylene composition to about room temperature.

15. A process for making propynyllithium, comprising contacting a mixture comprising propyne, allene, propane and butane with n-butyllithium in a mixed ethereal/hydrocarbon solvent under conditions sufficient to produce 1-propynyllithium.

16. A process for producing metallated acetylenes, comprising contacting an acetylenic compound or a mixture comprising an acetylenic compound and at least one saturated or unsaturated hydrocarbon which is different from said acetylenic compound with an organometallating agent in a hydrocarbon solvent under conditions sufficient to produce metallated acetylenic compound.

17. The process of claim 16, wherein said acetylenic compound is a compound according to the formula R—C≡CH, said organometallating agent is selected from the group consisting of organoalkali metals, organoalkaline earth metals, and organomagnesium halides, and said metallated acetylenic compound is a compound according to the formula R—C≡C—M, wherein R is hydrogen, alkyl, cycloalkyl, aryl, alkylaryl, arylalkyl, silyl, or heteroaromatic, and M is alkali metal or alkaline earth metal.

18. The process of claim 17, wherein said organometallating agent is an organoalkali metal compound of the formula $R^1$—M, wherein $R^1$ is alkyl, cycloalkyl, aryl, alkylaryl, or arylalkyl and M is alkali metal.

19. The process of claim 18, wherein each of R and $R^1$ is alkyl and M is lithium.

20. The process of claim 16, wherein said at least one saturated or unsaturated hydrocarbon is allene.

21. The process of claim 16, wherein said mixture further comprises at least one saturated C1 to C4 hydrocarbon.

22. The process of claim 21, wherein said C1 to C4 hydrocarbon is propane, butane, or a mixture thereof.

23. The process of claim 16, wherein said hydrocarbon solvent is selected from the group consisting of C5 to C10 alkane solvents, C5 to C10 cycloalkane solvents, C6 to C10 aromatic solvents, and mixtures thereof.

24. The process of claim 23, wherein said hydrocarbon solvent is hexane.

25. The process of claim 16, wherein said contacting step is conducted at a temperature of at least about 0° C.

26. A process for making 1-propynyllithium, comprising contacting propyne or a mixture comprising propyne and at least one saturated or unsaturated hydrocarbon which is different from propyne with n-butyllithium in a hydrocarbon solvent under conditions sufficient to produce 1-propynyllithium.

27. A process for making 1-propynyllithium, comprising contacting propyne or a mixture comprising propyne and at least one saturated or unsaturated hydrocarbon which is different from propyne with n-butyllithium in a hydrocarbon solvent at a temperature of at least about 0° C. to produce 1-propynyllithium.

28. A process for preparing acetylenic ketones, comprising:
   reacting metallated acetylenic compound and acid derivative or salt thereof to produce a reaction product comprising acetylenic ketone and unreacted reagents; and
   treating said reaction product under conditions sufficient to minimize formation of impurities by unreacted reagents present in said reaction product.

29. The process of claim 28, further comprising reacting transition metal halide with metallated acetylenic compound prior to the step of reacting metallated acetylenic compound with acid derivative.

30. The process of claim 28, further comprising after said treating step the step of recovering acetylenic ketone.

31. The process of claim 30, wherein the step of recovering acetylenic ketone comprises recovering acetylenic ketone of a purity of at least about 80%.

32. The process of claim 30, wherein the step of recovering acetylenic ketone comprises recovering acetylenic ketone of a purity of at least about 90%.

33. The process of claim 28, wherein said reaction product comprises unreacted acid derivative, and said treating step comprises neutralizing said unreacted acid derivative.

34. The process of claim 28, wherein said reacting step and said treating step are conducted at a temperature between about −20° C. and about 0° C.

35. The process of claim 28, wherein said treating step is conducted at a temperature between about −20° C. and about 0° C.

36. The process of claim 35, wherein the temperature of said reaction product is about −20° C. prior to said treating step, and wherein the temperature of said reaction product increases to about 0° C. during said treating step.

37. The process of claim 28, wherein said metallated acetylenic compound is a compound according to the formula R—C≡C—M, wherein R is hydrogen, alkyl, cycloalkyl, aryl, alkylaryl, arylalkyl, silyl, or heteroaromatic and M is alkali metal or alkaline earth metal, and said acid derivative is a compound according to the formula $R^2$COX, wherein $R^2$ is selected from the group consisting of alkyl, aryl, alkylaryl, arylalkyl, and cycloalkyl, and X is halogen, C1 to C10 alkoxy, anhydride, or $NR^3R^4$, wherein each $R^3$ and $R^4$ is independently selected from alkyl, aryl, alkylaryl, arylalkyl, cycloalkyl, C1 to C10 alkoxy, or $R^3$ and $R^4$ together represent a heterocyclic group.

38. The process of claim 37, wherein $R^2$ is alkylaryl and X is halide.

39. The process of claim 28, wherein said metallated acetylenic compound is 1-propynyllithium and said acid derivative is hydrocinnamoyl chloride.

40. The process of claim 29, wherein said transition metal halide is zinc chloride.

41. A process for preparing acetylenic ketones, comprising:
   reacting lithiated acetylenic compound, transition metal halide and acid halide at a temperature of about −20° C. to about 0° C. to produce a reaction product comprising acetylenic ketone and unreacted acid halide;
   neutralizing unreacted acid halide present in said reaction product at a temperature of about −20° C. to about 0° C.; and
   recovering acetylenic ketone from the reaction product.

42. A process for preparing 2-phenethyl 1-propynylketone (PPK), comprising:
   reacting 1-propynyllithium with zinc chloride and hydrocinnamoyl chloride at a temperature of about −20° C. to about 0° C. to produce a reaction product comprising PPK and unreacted hydrocinnamoyl chloride;
   neutralizing unreacted hydrocinnamoyl chloride in said reaction product at a temperature from about −20° C. to about 0° C.; and
   recovering PPK from said reaction product.

* * * * *